(12) United States Patent
Tupusheva

(10) Patent No.: US 12,128,225 B2
(45) Date of Patent: Oct. 29, 2024

(54) APPROACHES TO RESHAPING AND AUGMENTING SOFT TISSUE THROUGH LINEAR INJECTION OF DERMAL FILLERS

(71) Applicant: Nina Tupusheva, Austin, TX (US)

(72) Inventor: Nina Tupusheva, Austin, TX (US)

(73) Assignee: Nina Tupusheva, Austin, TX (US)

( * ) Notice: Subject to any disclaimer, the term of this patent is extended or adjusted under 35 U.S.C. 154(b) by 757 days.

(21) Appl. No.: 17/328,815

(22) Filed: May 24, 2021

(65) Prior Publication Data

US 2021/0361536 A1 Nov. 25, 2021

Related U.S. Application Data

(60) Provisional application No. 63/029,560, filed on May 25, 2020.

(51) Int. Cl.
*A61M 5/46* (2006.01)
*A61M 5/315* (2006.01)
*A61F 2/00* (2006.01)
*A61K 31/05* (2006.01)
*A61M 5/178* (2006.01)

(52) U.S. Cl.
CPC .......... *A61M 5/46* (2013.01); *A61M 5/31593* (2013.01); *A61F 2/0059* (2013.01); *A61K 31/05* (2013.01); *A61M 2005/1787* (2013.01); *A61M 2210/0625* (2013.01)

(58) Field of Classification Search
None
See application file for complete search history.

(56) References Cited

U.S. PATENT DOCUMENTS

2010/0057218 A1 * 3/2010 Burgess .................. A61L 27/52
623/23.72

FOREIGN PATENT DOCUMENTS

CN 113521446 A * 10/2021
RU 2736915 C1 * 11/2020
WO WO-2018231882 A1 * 12/2018 ............. A61K 35/35

* cited by examiner

*Primary Examiner* — Javier G Blanco
(74) *Attorney, Agent, or Firm* — Perkins Coie LLP; Andrew T. Pettit

(57) ABSTRACT

Introduced here are novel techniques for augmenting the lips through superficial linear injection of dermal fillers. At a high level, these techniques are representative of a two-step approach to augmentation. In the first stage, an implement that is appropriately positioned inside a lip can be moved sideways—an action referred to as a "side push." In the second stage, dermal filler can be ejected from the implement so as to fill the resulting void. These techniques can be used by healthcare professionals to reshape the lips for medical or aesthetic purposes. These techniques were developed in an attempt to permit augmentation of the outer surface of a lip so as to increase its volume by expanding sideways while turning the lip outward. With these techniques, the desired result—namely, a plumper lip—may be readily and consistently achievable.

12 Claims, 9 Drawing Sheets

"Type A"

Characterized by widely allocated philtrum columns and Cupid's bow. Both lips tend to be either wide or narrow.

"Type B"

Characterized by a narrow upper lip and wider lower lip. Lower lip may be visually turned inward. Closed lips generally do not fit tightly.

"Type C"

Characterized by lips that are inwardly tiled. Upper and lower lips are generally narrow. Closed lips generally do not fit tightly. Closed lips may form two holes, one to the left and one to the right of the central line.

FIGURE 1

| | Handheld Fan Form | Equilateral/Isosceles Triangle Form |
|---|---|---|
| First Entrance Point<br>Second Entrance Point<br>Third Entrance Point<br>Fourth Entrance Point<br>Fifth Entrance Point | Endpoint Boluses<br><br>Exit Bolus | Endpoint Boluses<br><br>Exit Bolus |
| | Handheld Fan Form<br>With Lateral Tunnel | Equilateral/Isosceles Triangle Form<br>With Lateral Tunnel |
| Sixth Entrance Point<br>Seventh Entrance Point | | |

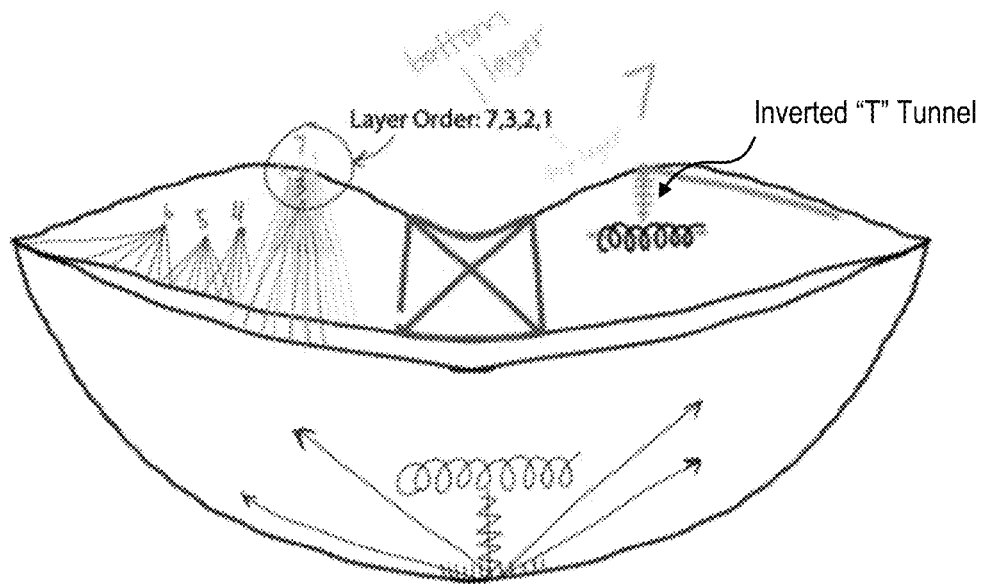

701 Create a first series of tunnels in the upper lip using the tip of a needle

702 Reinsert the tip of the needle through the first hole in the upper lip

703 Push the needle into a central tunnel of the first series of tunnels in the upper lip until the tip of the needle reaches a desired depth 704 Cause lateral movement of the tip of the needle toward the nearest oral commissure so as to form a first lateral tunnel 705 Inject dermal filler into the first lateral tunnel while withdrawing the tip of the needle though the first lateral tunnel and the central tunnel toward the first hole 706 Create a second series of tunnels in the upper lip using the tip of the needle 707 Reinsert the tip of the needle though the second hole in the upper lip 708 Cause movement of the tip of the needle along a portion of the vermilion border so as to form a second lateral tunnel 709 Inject dermal filler into the second lateral tunnel while withdrawing the tip of the needle through the second lateral tunnel toward the second hole

FIGURE 7

APPROACHES TO RESHAPING AND AUGMENTING SOFT TISSUE THROUGH LINEAR INJECTION OF DERMAL FILLERS

CROSS-REFERENCE TO RELATED APPLICATIONS

This application claims priority to US Provisional Application No. 63/029,560, titled "Technique of lips re-shaping and augmentation by mid to superficial linear (vector) injection of dermal filler" and filed on May 25, 2020, which is incorporated by reference herein in its entirety.

TECHNICAL FIELD

Various embodiments concern approaches to reshaping and augmenting soft tissue for medical or aesthetic purposes.

BACKGROUND

Traditionally, the lips have been viewed as symbols of sensuality and sexuality. For example, full lips will an accentuated border have been associated with beauty and youth. While the perceived ideal size of lips has varied over time across different cultures, communities across the world have introduced various materials into the upper and lower lips in an effort to enhance beauty.

Attempts to augment the lips through injection largely began in the early 20th century when surgeons began injecting paraffin into the lips without much success. Over the next several decades, other substances were used in an attempt to improve consistency, duration, and safety. For example, liquid silicone was used for augmentation starting in the 1960s but was largely abandoned in the 1990s due to concerns about the long-term effects on health. Bovine collagen was introduced to cosmetic surgery in the 1980s and quickly became the standard against which other substances were measured. However, because bovine collagen did not maintain its structure for very long once injected, it was gradually abandoned in favor of other alternatives.

With the surge in popularity of cosmetic surgery in the 1990s, additional substances—including biocompatible materials commonly used in other medical applications—became available for use in augmenting lips to have more attractive features. Some of the first widely used substances included autologous dermal material (also referred to as "autologen") made from the collagen of the recipient, donor dermal material (also referred to as "alloderm") made from the collagen of a cadaver, and synthetic dermal material produced in a laboratory. One example of a synthetic dermal material is Radiance, a solution that contains calcium hydroxylapatite suspended in a gel.

More options have been developed over the last several decades to make augmentation more effective and accessible. Some examples include:
  Fat Transfer: Healthcare professionals harvest fat from the recipient through liposuction or incision and then inject the fat into the lips.
  Gels: Clear gels that are reported to be close to the hyaluronic acid found naturally in the human body.
Healthcare professionals are continually looking to improve the substances and techniques used for augmentation. While significant advancements have been made, conventional substances and techniques do not permit healthcare professionals to augment the outer surface of a lip so as to increase its volume by expanding sideways while turning the lip outward.

BRIEF DESCRIPTION OF THE DRAWINGS

FIG. 1 illustrates three types of lips having different sizes, shapes, and locations of anatomical structures.

FIG. 3 includes a high-level illustration of a technique for augmenting "Type A" lips.

FIG. 7 is a flow diagram of another process for augmenting an upper lip.

Figure 2A:
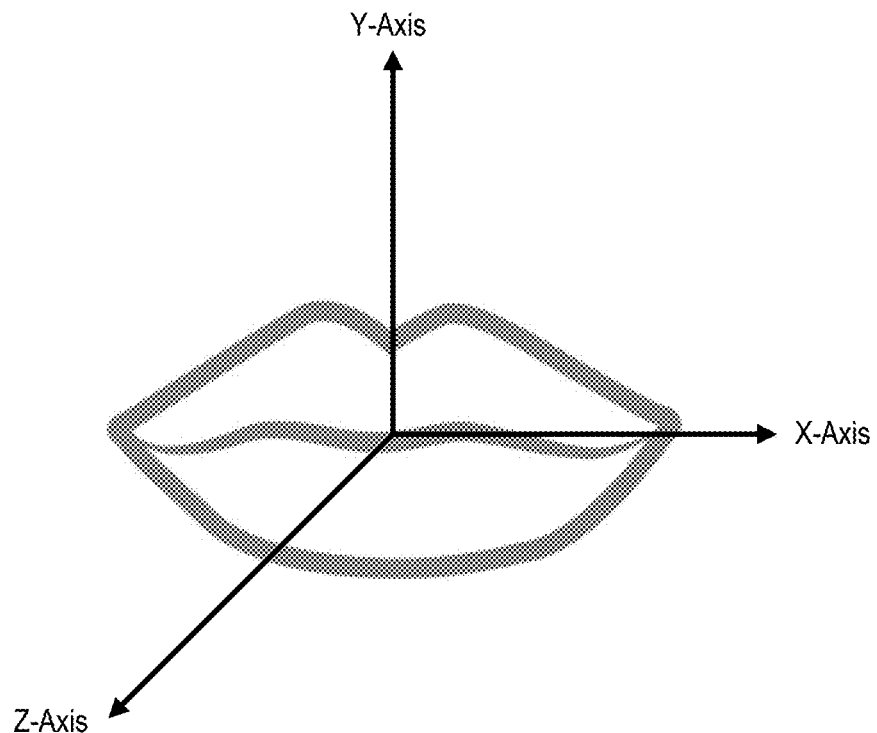
FIG. 2A illustrates how a Cartesian coordinate system may be used to describe movement of an implement with respect to the lips.

Various features of the techniques described herein will become more apparent to those skilled in the art from a study of the Detailed Description in conjunction with the drawings. Embodiments are illustrated by way of example and not limitation in the drawings. While the drawings depict various embodiments for the purpose of illustration, those skilled in the art will recognize that alternative embodiments may be employed without departing from the underlying principles of the techniques. Moreover, those skilled in the art will recognize that aspects of the lips may have been emphasized for illustrative purposes, and therefore may not be drawn to scale.

DETAILED DESCRIPTION

Introduced here are novel techniques for augmenting the lips through superficial linear injection of dermal fillers (also referred to as "lip augmentation fillers" or "substances"). Examples of dermal fillers include suspensions containing hyaluronic acid, polylactic acid, and polydioxanone. In some embodiments, dermal fillers may also contain, for example, autologous fat. For example, nano-grafts of fat ranging from 100 to 800 micrometer (μm) may be dispersed throughout the dermal filler to improve the likelihood of biocompatibility. As another example, platelet-rich plasma could be mixed into the dermal filter to improve the likelihood of biocompatibility.

At a high level, these techniques are representative of a two-step approach to augmentation. In the first stage, an implement that is appropriately positioned inside a lip can be moved sideways—an action referred to as a "side push." In the second stage, dermal filler can be ejected from the implement so as to fill the resulting void. These techniques can be used by healthcare professionals to reshape the lips for medical or aesthetic purposes. Note that the term "healthcare professional," as used herein, may refer to a plastic surgeon, dermatologist, physicians, nurses, and other individuals properly trained to perform augmentation, such as aestheticians, clinical laboratory technicians (CLTs), and the like. Accordingly, the term "healthcare professional" may be used interchangeably with the terms "injector" and "operator" of the implement.

These techniques were developed in an attempt to permit augmentation of the outer surface of a lip so as to increase its volume by expanding sideways while turning the lip outward. With these techniques, the desired result—namely, a plumper lip—may be readily and consistently achievable. As further discussed below, these techniques may not only allow a unique shape to be obtained but may also accomplish this using less filler than is normally used.

Embodiments may be described in the context of augmenting lips for the purpose of illustration. However, the approaches may be similarly applicable to augmenting any soft tissue located beneath the epidermis. For example, the approaches may be used to augment soft tissue located near the chin, cheeks, genitals, and the like.

Terminology

References in the present disclosure to "an embodiment" or "some embodiments" mean that the feature, characteristic, or action being described is included in at least one embodiment. Occurrences of such phrases do not necessarily refer to the same embodiment, nor are they necessarily referring to alternative embodiments that are mutually exclusive of one another.

The terms "comprise," "comprising," and "comprised of" are to be construed in an inclusive sense rather than an exclusive sense (i.e., in the sense of "including but not limited to"). The term "based on" is also to be construed in an inclusive sense rather than an exclusive sense. Thus, unless otherwise noted, the term "based on" is intended to mean "based at least in part on."

The term "implement" refers to any item that is capable of delivering a substance into a living body, for example, through injection. Examples of implements include needles (e.g., 27-, 29-, or 30-gauge needles) and cannulas.

The terms "central line," "central axis," and "line of symmetry" refer to the conditional line that splits the face vertically into two roughly symmetric parts, namely, a left part and right part.

The term "vector" refers to the conditional line of planned direction of the implement that pierces the lip and penetrates the underlying tissue. Multiple penetrations of the lip with the implement may result in a "set" of vectors. As further discussed below, the set of vectors may be representative of the penetrations through a single entrance point. Accordingly, the set of vectors may have a roughly triangular form. In embodiments where the ends of those vectors form a curve, the set of vectors may be said to resemble a handheld fan. Conversely, in embodiments where the ends of those vectors form a straight line, the set of vectors may be said to resemble an equilateral or isosceles triangle.

The term "tunnel" refers to the hollow space inside the lip formed by the implement penetrating the tissue.

The term "contour line" refers to the conditional line that goes alongside the contour of the lips, and thus is interchangeable with the term "vermillion border.".

The term "endpoint" refers to the deepest position of the implement within the tissue. At a high level, the endpoint represents the terminal end of the vector and tunnel.

The term "retrograde injection" refer to a known injection technique in which a substance is injected while the implement is retracted from the endpoint through the tissue.

The terms "positioned implement," "positioned needle," and "positioned cannula" refer to an implement, needle, or cannula that is appropriately positioned inside the tissue.

The term "duct" refers to a physiological feature inside tissue that is naturally formed and empty. Meanwhile, the term "p-duct" refers to a non-physiological formed feature inside tissue that is empty.

The term "gradient" refers to the angle of the implement measured with respect to a given axis (e.g., an x- or z-axis as discussed with reference to FIG. 2A).

The term "lateral" refers to movement that is generally in a sideways direction. Note that, unless otherwise specified, the term "lateral" does not imply that the movement is directly sideways. Thus, a "lateral" movement may occur anywhere along the xy-plane discussed with reference to FIG. 2A, rather than solely along the x-axis.

Structure and Anatomy

The upper and lower lips are referred to as the labium superius oris and labium inferius oris, respectively. The juncture where the lips meet the surrounding skin of the mouth area if referred to as the vermilion border, and the typically reddish area within the borders is referred to as the vermilion zone. The vermilion border of the upper lip is known as the Cupid's bow. The peaks of the "bow" coincide with the philtral columns giving a prominent bow appearance to the upper lip. These peaks may be referred to as the "Cupid's bow apex points" or "Glogau-Klein points" along the vermillion border. Each Cupid's bow apex point (or simply "apex point") corresponds to the slight elevation that represents a point of inflection as the upper lip turns from glabrous skin to mucosa. The fleshy protuberance located in the center of the upper lip is a tubercle known by various terms, including the procheilon, tuberculum labii superioris, and labial tubercle.

The skin of the lips, with 3 to 5 cellular layers, is relatively thin compared to the remained of the face, which may have up to 16 cellular layers. The skin of the lips also contains fewer melanocytes. The term "melanocytes" refers to the cells that produce melanin pigment. As such, the blood vessels tend to more readily appear through the skin of the lips, which results in the notable reddish coloring. At a high level, the skin of the lips forms the border between the exterior surface of the face and the mucous membrane of the inside of the mouth.

The lower lip is formed from the mandibular prominence, a branch of the first pharyngeal arch. The lower lip covers the anterior surface of the mandible. The lower lip is lowered by the depressor labii inferioris muscle, and the orbicularis oris borders the lower lip inferiorly.

Meanwhile, the upper lip covers the anterior surface of the maxilla. Its upper half has a depression at its center, directly under the nasal septum, called the philtrum, while its lower half is markedly different. The lower half is more similar in tone and texture to the inside of the mouth. The upper lip is raised by the levator labii superioris and is connected to the lower lip by the thin lining of the lip itself.

Classification Schemes

Lips can be classified as various types based on the size, shape, and location of the aforementioned anatomical structures. For the purpose of illustration, the techniques introduced here are described in the context of the three types of lips shown in FIG. 1. A first type ("Type A") is characterized by widely allocated philtrum columns and Cupid's bow. Both lips tend to either be wide or narrow. A second type ("Type B") is characterized by a narrow upper lip and wider lower lip. The lower lip may be visually turned inward, and when closed, the upper and lower lips generally do not fit together tightly. A third type ("Type C") is characterized by upper and lower lips that are inwardly tilted. Generally, the upper and lower lips are narrow, though this need not necessarily be true. When closed, the upper and lower lips generally do not fit together tightly. For example, closed lips may form two holes, one to the left and one to the right of the central line as shown in FIG. 1.

Overview of Spatial Coordinate System Governing Implement Movement

Rather than discussing movement of the implement with respect to the lips in absolute terms, it is helpful to discuss the techniques introduced here in terms of a spatial coordinate system. FIG. 2A illustrates how a Cartesian coordinate system may be used to describe movement of an implement with respect to the lips. Because the lips are described in terms of three-dimension (3D) space, the Cartesian coordinate system consists of an ordered triplet of lines (referred to as the "axes") that go through a common point (referred to as the "origin").

As shown in FIG. 2A, these axes may be x-axis, y-axis, and z-axis. The y-axis may be parallel to the central line that splits the face vertically into two roughly symmetric left and right parts, while the x-axis may be orthogonal to the central line. Thus, the x-axis may be representative of a horizontal line along which movement can be described as being either "left" or "right" with respect to the origin, and the y-axis may be representative of a vertical line along which movement can be described as being either "up" or "down" with respect to the origin.

A convention is to portray the xy-plane defined by the x- and y-axis horizontally. The z-axis may be added to represent "height" with respect to the xy-plane. Accordingly, if the x- and y-axis are shown as being horizontal and vertical, respectively, then the z-axis may be thought of as a conditional line that pointing down and to the left to indicate depth with respect to the xy-plane. At a high level, the z-axis may be helpful in terms of describing movement as "forward" or "backward" with respect to the origin. The term "forward" may refer to movement of an implement toward the back of the head, while the term "backward" may refer to movement of an implement away from the back of the head.

Another convention is to describe movements in terms of the planes along which those movements occur. Using the Cartesian coordinate system shown in FIG. 2A, the xy-plane may be parallel to the coronal plane (also referred to the "frontal plane") that divides the body into its dorsal and ventral parts, the xz-plane may be parallel to the transverse plane (also referred to as the "axial plane") that divides the body into its superior and inferior parts, and the yz-plane may be parallel to the sagittal plane (also referred to as the "longitudinal plane") that divides the body into its left and right parts. As an example, the phrase "along the sagittal plane" may be used to refer to a movement that occurs along the yz-plane, either toward the back or front of the head.

As further discussed below, the techniques described herein involve sideways movement of the implement while depth within the lip remains roughly constant. This is a non-standard movement that has not traditionally been performed while augmenting lips.

Figure 2B:
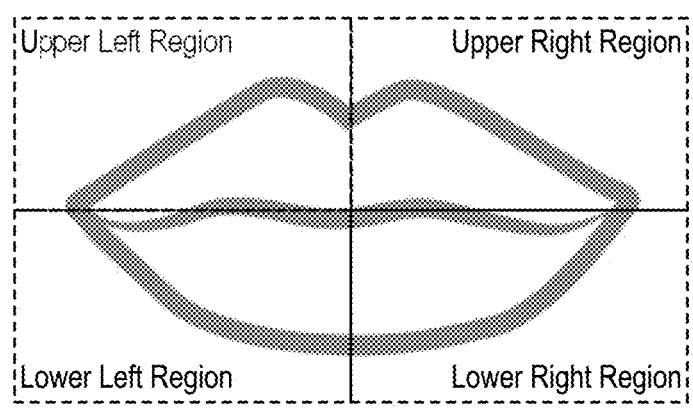
FIG. 2B illustrates how the Cartesian coordinate system of FIG. 2A allows the lips to be logically divided into separate regions.

FIG. 2B illustrates how the Cartesian coordinate system of FIG. 2A allows the lips to be logically divided into separate regions. These regions are largely defined using the central line that splits the face vertically into two roughly symmetric left and right parts. The upper left region may comprise the portion of the upper lip that is left of the central line from the perspective of the healthcare professional. The upper right region may comprise the portion of the upper lip that is right of the central line from the perspective of the healthcare professional. Similarly, the lower left region and lower right region may comprise the portions of the lower lip that are left and right of the central line, respectively, from the perspective of the healthcare professional.

Directional movement of an implement may also be described in the context of the Cartesian coordinate system. More specifically, directional movement of the implement may be described with reference to the xy-plane defined by the x- and y-axis. However, for simplicity, these movements may be described using the terms "north," "south," "east," and "west." The term "north" may refer to an upward vertical movement (e.g., an upward cut) of the implement, while the term "south" may refer to a downward vertical movement (e.g., a downward cut) of the implement. Said another way, the term "north" may refer to a movement along the y-axis in the positive direction, and the term "south" may refer to a movement along the y-axis in the negative direction. The term "east" may refer to a rightward horizontal movement (e.g., a rightward cut) of the implement, while the term "west" may refer to a leftward horizontal movement (e.g., a leftward cut) of the implement. Thus, the term "east" may refer to a movement along the x-axis in the positive direction, and the term "west" may refer to a movement along the x-axis in the negative direction.

These directional terms make it easier to describe movement that occurs along the x- and y-axis. For example, if the implement is moved upward and leftward, the implement may be said to be moving in the "northwest" direction. As another example, if the implement is moved upward and rightward, the implement may be said to be moving in the "northeast" direction. Downward movement can be described in a similar manner. Movements downward and leftward may be described as "southwest" movements, and movements downward and rightward may be described as "southeast" movements. For the purpose of illustration, directional movements may be described or shown at roughly 45 degrees from the x-axis. However, these terms are malleable. For example, the term "northeast" may be used to describe any directional movement occurring within the appropriate quadrant of the xy-plane (e.g., 15 degrees, 45 degrees, or 75 degrees with respect to the x-axis).

Example Technique for Type A Lips

Provided below is an example of a technique for augmenting "Type A" lips. This example is described in the context of a syringe with 1.0 cubic centimeter (cc) (1.0 milliliter) of dermal filler having a density of 20-24 milligrams per milliliter (mg/ml) of hyaluronic acid. The dermal filler did not include lidocaine, though it may include lidocaine or another local anesthetic in other embodiments. Moreover, the dermal filler may contain cannabidiol (also referred to as "CBD") in an amount no greater than 0.5 percent by weight. CBD may be included in lieu of, or in addition to, a local anesthetic. The syringe included a 27-gauge needle, though 29- or 30-gauge needles may be used in other embodiments. While the steps may be described in the context of a single syringe, those skilled in the art will recognize that multiple syringes could be used depending on the total amount of dermal filler that is required.

FIG. 3 includes a high-level illustration of the technique for augmenting "Type A" lips. At a high level, the purpose of the technique is to narrow the Cupid's bow and augment the lips so that the lips flatten outwards.

I. Shape Forming of Upper Lip

A. First Entrance Point

Initially, the needle can be located in the upper left region and then oriented in the south direction. The goal of the healthcare professional should be to select a point that is proximate to the philtrum column along the vermilion border that defines the Cupid's bow. Ideally, the point should be proximate to the apex zone of the Cupid's bow. Generally, the healthcare professional should avoid locating the needle near the central area (marked with an "X" in FIG. 3) to avoid causing edema and creating "duck lips" where the lips have a pursed appearance.

This point may be representative of the first entrance point into the upper lip. Generally, the depth of injection is not deep but also not superficial (e.g., approximately 2-4 mm, and preferably about 3 mm, deep), so the needle will not be visible through the skin while the tissue of the upper lip is tensioned. The healthcare professional may establish the appropriate depth by ensuring that the needle does not shine (e.g., due to reflection) through the skin of the upper lip.

When the needle reaches the border with the mucous membrane of the inside of the mouth, the healthcare professional can retract the needle and stop approximately 1 mm from the border. Said another way, the healthcare professional can move the needle backward along the tunnel until its end is approximately 1 mm from the border. While the healthcare professional should endeavor to locate the end of the needle near the border, it is important that the needle not pierce the mucous membrane.

Then, the healthcare professional can tension the skin of the upper lip (e.g., by pulling with her fingers) and then inject a small bolus of the dermal filler. The small bolus may be representative of a micro dose that is approximately 0.5-1.5 mm, and preferably about 1.0 mm, in size. The healthcare professional can then continually inject dermal filler along the entire length of the tunnel as the needle is drawn toward the first entrance point in the upper lip. That is, the healthcare professional can perform retrograde injection by injecting a small amount of the dermal filler as the needle is retracted. The pressure that must be applied to the plunger of the syringe will depend on the viscosity of the dermal filler, though the healthcare professional should only need to apply moderate pressure.

Once the end of the needle is near the first entrance point in the upper lip, the healthcare professional can insert the needle again rather than withdraw it from the upper lip. More specifically, the healthcare professional can repenetrate the tissue of the upper lip using an angle move with the lowest possible angle. Ideally, the healthcare professional should aim to shift the needle by approximately 5 degrees, though the shift may be larger or smaller than 5 degrees depending on the gauge size of the needle, dexterity of the healthcare professional, etc.

This process can be repeated several times so that a series of tunnels are created adjacent to one another. For example, this process may be repeated 3-9 times (and preferably 5-7 times) to fill separate tunnels with dermal filler via retrograde injection. The angle between the leftmost tunnel and rightmost tunnel should be within approximately 15-45 degrees. All movements of the needle should be linear vectors, so that the series of tunnels is along the same plane. Such an approach will "lift" the surface of the upper lip.

Before the needle is withdrawn from the upper lip through the first entrance point, the healthcare professional can inject another small bolus of the dermal filler. This small bolus may be roughly the same size as the small bolus injected near the endpoint of each tunnel. At a high level, this small bolus may serve to "cap off" the series of tunnels formed in the initial phase.

B. Second Entrance Point

The healthcare professional can then move the syringe leftward of the first entrance point. In order to narrow the Cupid's bow, the second entrance point should be located near the first entrance point. For example, the second entrance point may be located 1-3 mm (and preferably 2 mm) leftward of the first entrance point.

While the needle is oriented in the south direction, the healthcare professional can insert the needle into the upper lip and then perform a roughly similar procedure as discussed above with reference to the first entrance point to form a second series of tunnels. Because of the proximity of the first and second entrance points, the second series of tunnels may intersect the first series of tunnels. For example, the second series of tunnels may overlap roughly 50 percent of the first series of tunnels. Such an approach to injecting dermal filler will ensure that each consequent entrance point will lower the upper angle of the roughly triangular form.

C. Third Entrance Point

The healthcare professional can then move the syringe leftward and downward of the first and second entrance points. To establish the location of the third entrance point, the healthcare professional may locate the needle between the first and second entrance points and then move the needle leftward (e.g., by approximately 1-2 mm along the x-axis) and downward (e.g., by approximately 1-2 mm along the y-axis). The third entrance point is further from the vermilion border than the first and second entrance points.

While the needle is oriented in the south direction, the healthcare professional can insert the needle into the upper lip and then perform a roughly similar procedure as discussed above with reference to the first entrance point to form a third series of tunnels. Due to the location of the third entrance point with respect to the first and second entrance points, the third series of tunnels will begin to "push" the surface of the upper lip outward since it is layered on top of the first and second series of tunnels.

Again, the third series of tunnels can be defined such that inter-tunnel spacing is approximately 5 degrees. Depending on the number of tunnels included in the third series, the angle between the leftmost tunnel and rightmost tunnel may be approximately 15-45 degrees (and preferably 40-45 degrees with 8-9 tunnels). The vectors defined by the third series of tunnels may partially or entirely cover the vectors defined by the first and second series of tunnels.

D. Fourth Entrance Point

The healthcare professional can then move the syringe leftward and downward of the third entrance point. To establish the location of the fourth entrance point, the healthcare professional may locate the needle near the third entrance point and then move the needle leftward (e.g., by approximately 1-2 mm along the x-axis) and downward (e.g., by approximately 1-2 mm along the y-axis). Again, while the needle is oriented in the south direction, the healthcare professional can insert the needle into the upper lip and then perform a roughly similar procedure as discussed above with reference to the first entrance point to form a fourth series of tunnels.

E. Fifth Entrance Point

There is a blood vessel located along the outer edge of the upper lip near the surface of the skin. To avoid occlusion and penetration of this blood vessel, the last entrance point may be located approximately 0.5-1.5 centimeters (cm) inward from the mouth angle (also referred to as the "oral commissure"). Moreover, the healthcare professional may turn the syringe so that the needle is oriented toward the mouth angle. Said another way, the healthcare professional may start with the needle oriented in the south direction and then gradually change each vector until the needle is oriented in the southwest direction. After the healthcare professional has reached the final needle tip position—which will be nearest to the mouth angle—she can begin to allocate dermal filler and then evenly fill the tunnel while exiting the fifth entrance point.

While the sequences of steps discussed with reference to the first through fifth entrance points are exemplary, the steps may be performed in various sequences and combinations unless contrary to physical possibility. For example, if the upper lip is wide (e.g., greater than 4.5 cm, 4.75 cm, or 5 cm in width), the process described above with reference to the fourth entrance point could be repeated multiple times until the healthcare professional approaches the outermost edge of the upper lip. Accordingly, there may be more five separate entrance points.

These steps could then be repeated for the upper right region so as to create multiple series of tunnels along the right side of the upper lip.

II. Shape Fixing of Upper Lip

By injecting dermal filler into the left and right sides of the upper lip as discussed above, the healthcare professional can form a new lip shape. This shape must be fixed, however, as its natural appearance may be nonuniform and unnatural.

Initially, a needle can be located in the upper left region and then oriented in the south direction. To start, the healthcare professional may use the first entrance point or second entrance point. After inserting the needle, the healthcare professional can push downward until the needle reaches roughly the middle of the upper lip.

Then, the healthcare professional can move the needle sideways along the xz-plane. For example, the healthcare professional may apply a lateral force to the syringe so as to cause the needle to shift or rotate outward toward the mouth angle. Note that the depth of the needle in the upper lip may not change while sideways movement occurs. Thereafter, the healthcare professional can push the needle inward along the z-axis (e.g., by approximately 2-4 mm) and then stretch the tissue by tensioning the upper lip (e.g., with her fingers). As this occurs, dermal filler can be injected into the vector that is formed upon exit of the needle. When the needle is moved along the z-axis, an indentation will form beneath the needle. Dermal filler can be injected as this indentation is formed. The dermal filler will expand sideways to occupy the space formed by the sideways movement of the needle.

Such an approach will result in a filler-filed tunnel that has the form of an inverted "T." This will alter the peak of the Cupid's bow, forming a new peak and opening the upper lip outward.

Moreover, the healthcare professional may insert the syringe through the last entrance point formed in the upper lip and then move the needle alongside the contour line. For example, the healthcare professional may move the needle in parallel to the contour line (e.g., approximately 1-2 mm on x-axis and 1-2 mm on y-axis) across the entire length of the corresponding series of tunnels and then apply dermal filler upon withdrawal of the needle via retrograde injection. After filling the last tunnel near the periphery of the upper lip, the mouth angle will slightly rise.

If this rise is insufficient to achieve the desired same, the healthcare professional can perform the process again, using the same entrance point in order to make another vector at a lower level. For example, a new vector may be made approximately 5 degrees lower than the existing vector. This is not always necessary, however. In some instances, the rise will be sufficient after a single rise. Note that before the needle is withdrawn from the upper lip, a small bolus may be injected near the endpoint of the corresponding tunnel.

Forming and then shaping the upper lip in this manner will result in the peaks of the upper lip becoming narrower. The tunnels formed via the first, second, and third entrance points will essentially create a new peak of the Cupid's bow by moving it toward the center. Meanwhile, the tunnels formed via the sixth and seventh entrance points (i.e., the inverted "T" tunnels) can be used to alter the shape of the upper lip by adjusting the location of the triangular peak of the Cupid's bow. As discussed above, the sixth entrance point may be the first entrance point or second entrance point, and the seventh entrance point may be the fifth entrance point.

In order to avoid destruction of this newly formed structural frame comprised of dermal filler inside the upper lip, the healthcare professional may refrain from massaging the upper lip. Similarly, the healthcare professional may instruct the recipient (also referred to as the "patient") to avoid massaging the upper lip. Generally, it takes roughly 2-4 weeks for the dermal filler to settle. Accordingly, care should be taken not to affect the upper lip during that timeframe, especially at night, in order to preserve the shape. The overall quantity of filler for the upper lip is normally about 0.4 cc (i.e., about 0.2 cc for each side).

III. Shape Forming and Fixing of Lower Lip

To augment the lower lip, the healthcare professional can orient the syringe in the north direction so that the needle is centrally located between the lower left and right regions. At a high level, the healthcare professional should aim to locate the needle near the vermilion border of the lower lip along the central line. The healthcare professional can then insert the needle roughly halfway into the lower lip.

Then, the healthcare professional can push the needle inward so that it moves toward the back of the head along the z-axis (e.g., by 2-5 mm) and then stretch the tissue by tensioning the lower lip (e.g., with her fingers). This will result in formation of a tunnel roughly along the z-axis. This tunnel may be referred to as a "horizontal tunnel." When the needle is pushed along the z-axis, an indentation will form beneath the needle. Dermal filler can be injected as this indentation is formed. Thereafter, the healthcare professional can withdraw the needle along the tunnel—while still tensioning the lower lip—and apply dermal filler via retrograde injection. Before the needle is withdrawn from the lower lip, a small bolus may be injected near the entrance point.

Injections made in accordance with the technique described above may be made in micro doses only. Accordingly, the total quantity of dermal filler in the lower lip may only be about 0.2 cc.

Example Technique for Type B Lips

Provided below is an example of a technique for augmenting "Type B" lips. This example is described in the context of a syringe with 1.0 cc (1.0 ml) of dermal filler having a density of 20-24 mg/ml of hyaluronic acid. The dermal filler did not include lidocaine, though it may include lidocaine or another local anesthetic in other embodiments. Moreover, the dermal filler may contain cannabidiol (also referred to as "CBD") in amount no greater than 0.5 percent by weight. CBD may be included in lieu of, or in addition to, a local anesthetic. The syringe included a 27-gauge needle, though 29- or 30-gauge needles may be used in other embodiments. While the steps may be described in the context of a single syringe, those skilled in the art will recognize that multiple syringes could be used depending on the total amount of dermal filler that is required.

Figure 4:
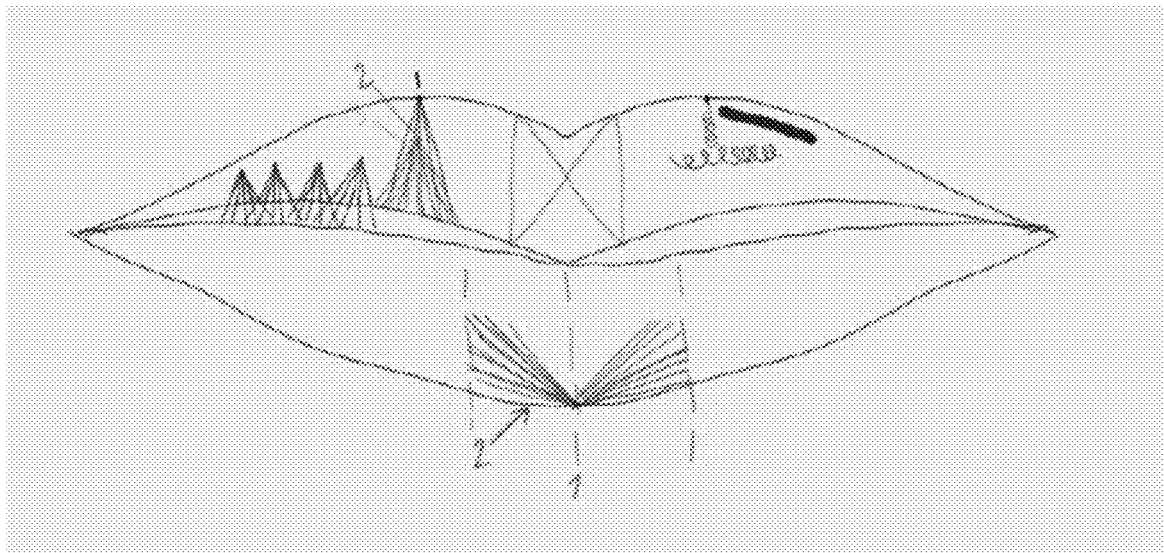
FIG. 4 includes a high-level illustration of a technique for augmenting "Type B" lips.

FIG. 4 includes a high-level illustration of the technique for augmenting "Type B" lips. At a high level, the purpose of the technique is to augment the upper lip so as to fill in gaps in the underlying tissue. Again, the healthcare professional should avoid working in the central area to avoid causing edema and creating "duck lips" where the lips have a pursed appearance.

I. Shape Forming of Upper Lip

A. First Entrance Point

Initially, the needle can be located in the upper left region proximate to the peak of the Cupid's bow. This is where the first entrance point will be located. While the needle is oriented in the south direction, the healthcare professional can insert the needle through the upper lip. Generally, the depth of injection is not deep but also not superficial, so the needle will not be visible through the skin while the tissue of the upper lip is tensioned. The healthcare professional may establish the appropriate depth by ensuring that the needle does not shine (e.g., due to reflection) through the skin of the upper lip.

When the needle reaches the border with the mucous membrane of the inside of the mouth, the healthcare professional can retract the needle and stop approximately 1 mm from the border. Said another way, the healthcare professional can move the needle backward along the tunnel until its end is approximately 1 mm from the border. While the healthcare professional should endeavor to locate the end of the needle near the border, it is important that the needle not pierce the mucous membrane.

Then, the healthcare professional can tension the skin of the upper lip (e.g., by pulling with her fingers) and then inject a small bolus of the dermal filler. The small bolus may be representative of a micro dose that is approximately 1-3 mm, and preferably about 2 mm, in size. The healthcare professional can then continually inject dermal filler along the entire length of the tunnel as the needle is drawn toward the first entrance point in the upper lip. That is, the healthcare professional can perform retrograde injection by injecting a small amount of the dermal filler as the needle is retracted. The pressure that must be applied to the plunger of the syringe will depend on the viscosity of the dermal filler, though the healthcare professional should only need to apply moderate pressure.

Once the end of the needle is near the first entrance point in the upper lip, the healthcare professional can insert the needle again rather than withdraw it from the upper lip. More specifically, the healthcare professional can repenetrate the tissue of the upper lip using an angle move with the lowest possible angle. Ideally, the healthcare professional should aim to shift the needle by approximately 5 degrees, though the shift may be larger or smaller than 5 degrees depending on the gauge size of the needle, dexterity of the healthcare professional, etc.

This process can be repeated several times so that a series of tunnels are created adjacent to one another. For example, this process may be repeated 3-9 times (and preferably 5-7 times) to fill separate tunnels with dermal filler via retrograde injection. The angle between the leftmost tunnel and rightmost tunnel should be within approximately 15-45 degrees. All movements of the needle should be linear vectors, so that the series of tunnels is along the same plane. Such an approach will "lift" the surface of the upper lip.

Before the needle is withdrawn from the upper lip through the first entrance point, the healthcare professional can inject another small bolus of the dermal filler. This small bolus may be roughly the same size as the small bolus injected near the endpoint of each tunnel. At a high level, this small bolus may serve to "cap off" the series of tunnels formed in the initial phase.

B. Second Entrance Point

The healthcare professional can then move the syringe downward of the first entrance point along the y-axis. For example, the second entrance point may be located 1-3 mm (and preferably 2 mm) lower than the first entrance point along the same vertical line. While the needle is oriented in the south direction, the healthcare professional can insert the needle into the upper lip and then perform a roughly similar procedure as discussed above with reference to the first entrance point to form a second series of tunnels. The number of tunnels need not be identical, however. For example, the second series may only include 5-6 tunnels while the first series may include 5-7 tunnels.

C. Additional Entrance Points

Whether more than two entrance points are necessary largely depends on whether a lack of volume in the upper lip is still visually noticeable. If the healthcare professional still observes a lack of volume after injecting dermal filler into the second series of tunnels, then she can create a third entrance point in the upper lip. For example, the healthcare professional can move the syringe leftward (e.g., by approximately 1-2 mm along the x-axis) and downward (e.g., by approximately 1-2 mm along the y-axis) from the second entrance point. While the needle is oriented in the south direction, the healthcare professional insert the needle into the upper lip and then perform a roughly similar procedure as discussed above with reference to the first entrance point to form a third series of tunnels.

This step can be repeated as many times as necessary to provide volume to the upper lip. Generally, the number of times that this step must be repeated (and thus, the number of entrance points that must be formed) will depend on the dimensions of the upper lip.

To move the lateral part of the upper lip outward, the healthcare professional can make an entrance point proximate to the contour line. Using this entrance point, the healthcare professional can create a vertical vector that extends toward the border of the mucous membrane but stops approximately 1 mm short of the border. The healthcare professional can then perform retrograde injection so as to fill the tunnel with dermal filler as the needle is withdrawn toward the entrance point. If the healthcare professional determines that the outward turn of the upper lip is insufficient, then she can form another tunnel by performing an angle move. Dermal filler can be injected into this tunnel via retrograde injection as the needle is withdrawn toward the entrance point. While a single tunnel may be sufficient to achieve outward turn of the upper lip, a series of tunnels are shown in FIG. 4 for the purpose of illustration. This series of tunnels is labeled using the reference numeral 4.

In order to lift the mouth angle, the healthcare professional may request that the recipient hold her lips as if uttering the "O" sound. Then, the healthcare professional can make an entrance point proximate to the vermilion border of the upper lip through the oral commissure. Through this entrance point, the healthcare professional can internally contour the upper lip in the upper left region. However, the needle does not need to be very deep. While withdrawing the needle, dermal filler can be injected via retrograde injection, thereby forming a bridge between the upper and lower lips.

These steps could then be repeated in the upper right region so as to create multiple series of tunnels along the right side of the upper lip.

II. Shape Fixing of Upper Lip

To shape the upper lip, the healthcare professional can perform similar steps as those discussed above with reference to FIG. 3. Initially, a needle can be located in the upper left region and then oriented in the south direction. To start, the healthcare professional may use the first entrance point or second entrance point. After inserting the needle, the healthcare professional can push downward until the needle reaches roughly the middle of the upper lip.

Then, the healthcare professional can push the needle inward along the z-axis (e.g., by approximately 2-4 mm) and then stretch the tissue by tensioning the upper lip (e.g., with her fingers). As this occurs, dermal filler can be injected into the vector that is formed upon exit of the needle. When the needle is moved along the z-axis, an indentation will form beneath the needle. Dermal filler can be injected as this indentation is formed. The dermal filler will expand sideways to occupy the space formed by the sideways movement of the needle. Such an approach will result in a filler-filed tunnel that has the form of an inverted "T." This will alter the peak of the Cupid's bow, forming a new peak and opening the upper lip outward.

The overall quantity of filler for the upper lip is about 0.8 cc (i.e., about 0.4 cc for each side). Moreover, a small amount of dermal filler (e.g., approximately 0.2 cc) may be reserved for correction over the next 10-14 days as the shape settles into its final form.

III. Shape Forming and Fixing of Lower Lip

Before augmenting the lower lip, the healthcare professional may visually split the lower lip into three parts of roughly equal length, namely, a left portion, central portion, and right portion. As shown in FIG. 4, augmentation of the lower lip may be limited to the central portion. With the syringe oriented in the northwest direction, the healthcare professional can centrally locate the needle between the lower left and right regions. At a high level, the healthcare professional should aim to locate the needle near the vermilion border of the lower lip along the central line. The healthcare professional can then create a series of tunnels covering the entire width of the lower lip. To create the next tunnel, the healthcare professional can move the syringe in either the west direction, thereby creating tunnels that are increasingly closer to the vermilion border of the lower lip. This series of tunnels normally includes 8-12 tunnels, though more or less may be included in some embodiments. Depending on the number of tunnels, the angle between the leftmost tunnel and rightmost tunnel may be approximately 20-50 degrees (and preferably 30-40 degrees).

Without exiting the entrance point, the healthcare professional can then orient the syringe in the northeast direction. The same process can be repeated so as to form another series of tunnels in the lower lip. However, to create each tunnel, the healthcare professional may move the syringe in the east direction; again, creating tunnels that are increasingly closer to the vermilion border of the lower lip. Before the needle is withdrawn from the lower lip, a small bolus may be injected near the entrance point.

Often, these tunnels will provide sufficient structure to the lower lip. However, if the healthcare professional determines that the volume of the lower lip is insufficient, then she can move the syringe leftward (e.g., by approximately 1-2 mm along the x-axis) and upward (e.g., by approximately 1-2 mm along the y-axis) and then create another entrance point. A similar process may be performed to locate dermal filler beneath the series of tunnels formed using the first entrance point in the lower lip.

Example Technique for Type C Lips

Provided below is an example of a technique for augmenting "Type C" lips. This example is described in the context of a syringe with 1.0 cc (1.0 ml) of dermal filler having a density of 20-24 mg/ml of hyaluronic acid. The dermal filler did not include lidocaine, though it may include lidocaine or another local anesthetic in other embodiments. Moreover, the dermal filler may contain cannabidiol (also referred to as "CBD") in amount no greater than 0.5 percent by weight. CBD may be included in lieu of, or in addition to, a local anesthetic. The syringe included a 27-gauge needle, though 29- or 30-gauge needles may be used in other embodiments. While the steps may be described in the context of a single syringe, those skilled in the art will recognize that multiple syringes could be used depending on the total amount of dermal filler that is required.

Figure 5:
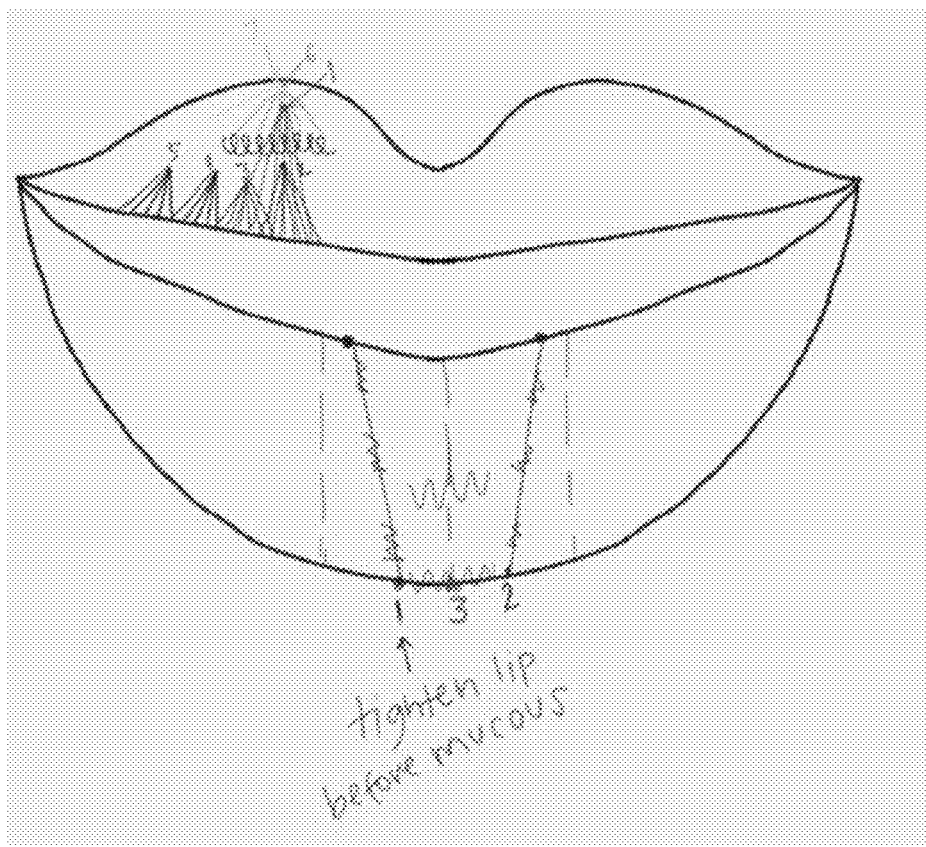
FIG. 5 includes a high-level illustration of a technique for augmenting "Type C" lips.

FIG. 5 includes a high-level illustration of the technique for augmenting "Type C" lips. The technique is generally similar to those discussed with reference to FIGS. 3-4, so only select aspects of the technique have been described in detail.

I. Shape Forming and Fixing of Upper Lip

Initially, a healthcare professional can locate the needle of a syringe in the upper left region and then orient the needle in the south direction. The first entrance point may be located approximately one-quarter of the upper lip width from the peak of the Cupid's bow. The healthcare professional can then create a first series of tunnels (e.g., 8-12 tunnels in total), each of which may extend roughly two-thirds of the way toward the border of the mucous membrane of the inside of the mouth.

The second entrance point may be located approximately one-half of the upper lip width from the peak of the Cupid's bow. Thus, the second entrance point may be located along the same vertical line as the first entrance point, but further downward along the y-axis. Via the second entrance point, the healthcare professional can create a second series of tunnels (e.g., 6-8 tunnels in total), each of which may extend nearly all the way to the border of mucous membrane.

Several more entrance points can then be created. For example, the healthcare professional may create third, fourth, and fifth entrance points by successively locating the needle closer to the mouth angle as shown in FIG. 5. These entrance points may be arranged such that a visual line that extends from the second entrance point to the oral commissure passes through the third, fourth, and fifth entrance points. Each entrance point may be associated with a corresponding series of tunnels (e.g., 6-8 tunnels in total).

The sixth entrance point may be located near the peak of the Cupid's bow. Via the sixth entrance point, the healthcare professional can create a sixth series of tunnels (e.g., 8-12 tunnels) whose length extends over the first series of tunnels. At a high level, the sixth series of tunnels may be representative of a structural layer beneath the first series of tunnels that serves to push the surface of the upper lip outward. Like the first, second, third, fourth, and fifth series of tunnels, the sixth series of tunnels can be filled with dermal filler via retrograde injection as the needle is withdrawn from each tunnel.

Without exiting the sixth entrance point, the healthcare professional can move the needle laterally into the hollow duct. Once there, the healthcare professional can inject dermal filler via retrograde injection, thereby forming an inverted "T." Moreover, the healthcare professional may insert the needle alongside the lip contour until reaching the utmost position near the oral commissure. This tunnel can also be filled with dermal filler via retrograde injection. Before the needle is withdrawn from the upper lip through the sixth entrance point, the healthcare professional can inject a small bolus of the dermal filler.

II. Shape Forming and Fixing of Lower Lip

With the syringe oriented in the north direction, the healthcare professional can centrally locate the needle between the lower left and right regions. At a high level, the healthcare professional should aim to locate the needle near the vermilion border of the lower lip along the central line. Then, the healthcare professional can set a first visual line vertically about 1 cm left of the central line and a second visual line vertically about 1 cm right of the central line.

The healthcare professional can then make a first entrance point through the first visual line and create a first tunnel that starts at the edge of the contour line and extends nearly to the border of the mucous membrane. As shown in FIG. 5, this first tunnel will be angled toward the various entrance points in the upper left region. This first tunnel can then be filled with dermal filler via retrograde injection.

Similarly, the healthcare professional can make a second entrance point through the second visual line and create a second tunnel that starts at the edge of the contour line and extends nearly to the border of the mucous membrane. As shown in FIG. 5, this second tunnel will be angled toward the various entrance points in the upper right region. This second tunnel can then be filled with dermal filler via retrograde injection.

Together, the first and second tunnels allows a dimple to form in the center of the lower lip. Overall, this has the effect of turning the lower lip outwards as intended.

Methodologies for Upper and Lower Lip Augmentation

The techniques introduced here represent a novel way of reshaping or augmenting lips through mid to superficial injection of dermal filler. In contrast to conventional approaches, the techniques allow lips to be augmented laterally (e.g., to flatten the surface of the lips). Using the techniques, it is possible to form not only the classical shapes discussed above, but also new and unusual shapes (e.g., an inverted pentagonal shape, hexagonal shape, heptagonal shape, octagonal shape).

Figure 6:
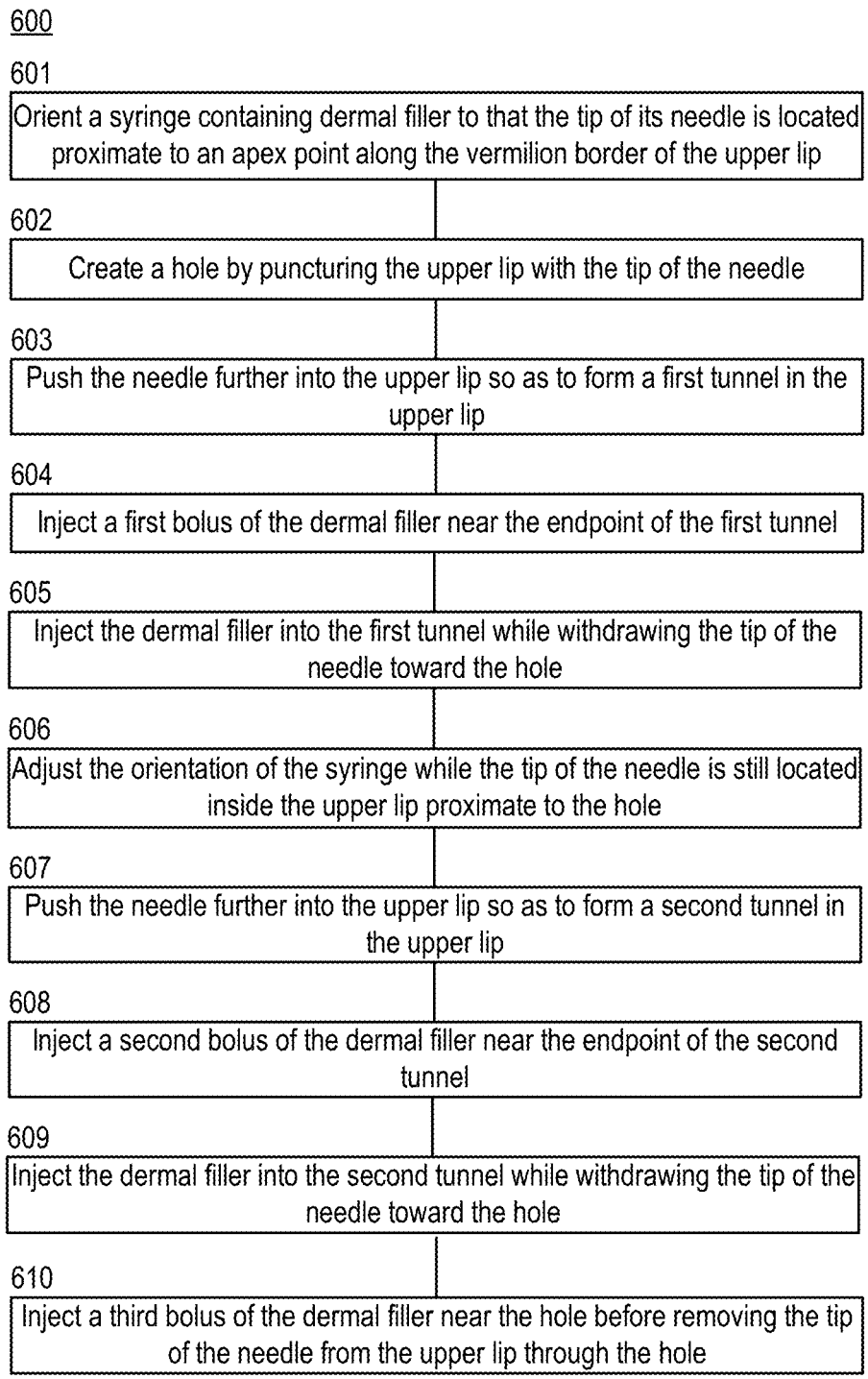
FIG. 6 includes a flow diagram of a process for augmenting an upper lip.

While the techniques have been described in great depth above with reference to the various examples, several flow diagrams covering select aspects of the techniques are shown in FIGS. 6-7.

FIG. 6 includes a flow diagram of a process 600 for augmenting an upper lip. This process 600 is focused on the initial stage of forming vertical tunnels that, when filled with dermal filler, provide structure to the upper lip. Initially, a healthcare professional can orient a syringe containing dermal filler so that the tip of its needle is located proximate to an apex point of the Cupid's bow formed by a vermilion border of the upper lip (step 601). Said another way, the healthcare professional can orient the syringe so that the tip of its needle is located near one of the crests of the Cupid's bow formed by the vermilion border. Then, the healthcare professional can create a hole by puncturing the upper lip with the tip of the needle (step 602). A local anesthetic may be applied to the upper lip before the hole is formed in some embodiments. Local anesthetic may be helpful in ensuring that minimal movement occurs as the procedure occurs. Additionally or alternatively, the dermal filler contained in the syringe may include a substance that alleviates pain or relaxes the tissue inside the upper lip. For example, the dermal filler may contain small amounts of CBD.

The healthcare professional can then push the needle further into the upper lip so as to form a first tunnel in the upper lip (step 603). Once the tip of the needle reaches the desired depth, the healthcare professional may inject a small bolus of the dermal filler. Thus, the healthcare professional may inject a first bolus of the dermal filler near the endpoint of the first tunnel (step 604). Moreover, the healthcare professional can inject dermal filler into the first tunnel while withdrawing the tip of the needle toward the hole (step 605). This technique is referred to as "retrograde injection" since dermal filler is injected while the needle is being slowly withdrawn.

As discussed above, the healthcare professional may withdraw the needle until its tip is located near the hole. The tip may not actually be removed from the hole, however. Instead, the healthcare professional may adjust the orientation of the syringe while the tip of the needle is still located inside the upper lip proximate to the hole (step 606). Then, the healthcare professional can repeat the above-mentioned steps to create another tunnel. Thus, the healthcare professional may push the needle further into the upper lip so as to form a second tunnel in the upper lip (step 607). Once the tip reaches the desired depth, the healthcare professional may inject a small bolus of the dermal filler. Thus, the healthcare professional may inject a second bolus of the dermal filler near the endpoint of the second tunnel (step 608). Moreover, the healthcare professional can inject dermal filler into the second tunnel while withdrawing the tip of the needle toward the hole (step 609).

By performing these steps repeatedly, the healthcare professional can form a series of tunnels that emanate from the hole. Normally, the series of tunnels includes 5-7 tunnels, though embodiments may include fewer than 5 tunnels or greater than 7 tunnels. Moreover, while the healthcare professional may repeatedly adjust the orientation of the syringe to form the series of tunnels along different vectors, the actual adjustment may be small. For example, the healthcare professional may try to ensure that the angle between neighboring tunnels is no more than 5-10 degrees. Accordingly, the entire series of tunnels may have a spread of no more than 30-50 degrees. For example, if the healthcare professional creates 10 separate tunnels with inter-tunnel spacing of approximately 5 degrees, then the total spread may be approximately 45 degrees.

Before the needle is entirely removed from the upper lip, the healthcare professional may inject another small bolus that serves to "cap off" the series of tunnels. Accordingly, the healthcare professional may inject a third bolus of the dermal filler near the hole before removing the tip of the needle from the upper lip through the hole (step 610).

FIG. 7 is a flow diagram of another process 700 for augmenting an upper lip. This process 700 is focused on the secondary stage of forming lateral tunnels that, when filled with dermal filler, can be used to form or adjust the shape of the upper lip. Initially, a healthcare professional can create a first series of tunnels in the upper lip (step 701). As discussed above with reference to FIG. 6, this can be accomplished by locating the tip of the needle proximate to the Cupid's bow apex point along the vermilion border of the upper lip, puncturing the upper lip with the tip of the needle so as to form a first hole, and then pushing the needle further into the upper lip repeatedly along different vectors so as to form the first series of tunnels. These vectors may vary only slightly in spatial direction. For example, the angle between a given tunnel and a neighboring tunnel that was formed prior to the given tunnel may be the lowest possible angle that is achievable by the healthcare professional without affecting structural integrity of the neighboring tunnel. Normally, the angle between neighboring tunnels is approximately 5-10 degrees.

Generally, the first series of tunnels are arranged along a single plane. This is important because, in some embodiments, the first series of tunnels is one of multiple series of tunnels that are located close to one another in the same region of the upper lip. Locating all of the tunnels in each series along a single plane helps to ensure that these various series of tunnels do not intersect, at least to a significant degree.

Thereafter, the healthcare professional may reinsert the tip of the needle through the first hole in the upper lip (step 702). The healthcare professional can then push the needle into a central tunnel of the first series of tunnels in the upper lip until the tip of the needle reaches a desired depth (step 703). This desired depth may correspond to the endpoint of the central tunnel. Thus, the healthcare professional may push the needle until she estimates that the tip of the needle is proximate to the endpoint of the central tunnel.

The healthcare professional can then cause lateral movement of the tip of the needle toward the nearest oral commissure so as to form a first lateral tunnel (step 704). For example, if the needle is inserted into the upper lip in the upper left region, then the healthcare professional may cause lateral movement of the tip of the needle toward the oral commissure located between the upper and lower left regions. Lateral movement of the tip of the needle may be achieved by applying a lateral force to the syringe of which the needle is a part. At a high level, the healthcare professional may rotate the syringe (and thus the needle) about the first hole in the upper lip. Note that while lateral movement occurs, the depth of the tip of the needle (e.g., in terms of the z-axis) may not change.

The healthcare professional can then inject dermal filler into the first lateral tunnel while withdrawing the tip of the needle through the first lateral tunnel and the central tunnel toward the first hole (step 705). When filled with dermal filler, this lateral tunnel provides support to the upper lip as it is roughly orthogonal to each tunnel included in the first series of tunnels. As mentioned above, the healthcare professional may tension the upper lip while the dermal filler is injected into the first lateral tunnel in some embodiments. For example, the healthcare professional may use her fingers to stretch the upper lip, thereby tensioning the tissue inside the upper lip.

Additional steps may also be performed in some embodiments. For example, the healthcare professional may create a second series of tunnels in the upper lip (step 706). This can be accomplished by locating the tip of the needle nearer the nearest oral commissure than the first hole, puncturing the upper lip with the tip of the needle so as to form a second hole, and then pushing the needle further into the upper lip repeatedly along different vectors so as to form the second series of tunnels. Normally, the second series of tunnels is formed substantially contemporaneously with the first series of tunnels. While steps 702-705 are normally performed after step 706 in practice, that need not necessarily be the case.

Thereafter, the healthcare professional may reinsert the tip of the needle through the second hole in the upper lip (step 707). The healthcare professional can then cause movement of the tip of the needle along a portion of the vermilion border so as to form a second lateral tunnel (step 708). Then, the healthcare professional may inject dermal filler into the second lateral tunnel while withdrawing the tip of the needle through the second lateral tunnel toward the second hole (step 709). The portion of the vermilion border may correspond to the entire width of the second series of tunnels. Accordingly, when filled with dermal filler, this second lateral tunnel may provide support to the upper lip as it is roughly orthogonal to each tunnel included in the second series of tunnels.

Facilitating Injection of Dermal Filler

Figure 8:
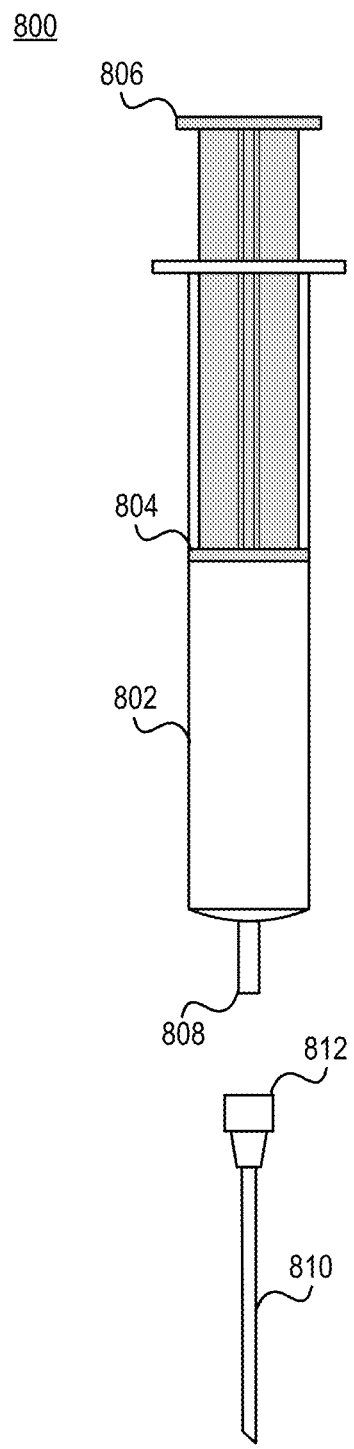
FIG. 8 includes an illustration of a conventional syringe.

As mentioned above, syringes have traditionally been used to inject dermal filler the lips. FIG. 8 includes an illustration of a conventional syringe 800. At a high level, the syringe 800 includes a durable barrel 802 that usually has graduated marks indicating the volume of fluid in the syringe 800, a piston 804 located inside the barrel 802, and a plunger 806 for moving the piston 804. At the end of the barrel 802, there is a tip 808 to which a needle 810 (and, more specifically, a needle hub 812) can be connected. While the barrel 802 is nearly always transparent, the barrel 802 may be comprised of various materials. For example, the barrel 802 may be comprised of plastic or glass depending on how the syringe 800 is to be used, sterilized, stored, etc. Similarly, the plunger 806 and piston 804 may be comprised of various materials, though those components are increasingly being made from plastic or rubber to make disposal after a single use more practical (and less costly).

There are a number of different designs for the area in which the needle hub 812 connects to the tip 808 of the barrel 802. The most well-known of these designs is the Luer lock, which simply requests that the components be twisted together. Meanwhile, components featuring plain connections may be referred to as "slip tips." Such a design may be useful when the tip 808 of the barrel 802 is being connected to a needle hub 812 that does not include a screw lock mechanism.

Conventional syringes are useful in various contexts. However, there are several reasons that conventional syringes are impractical for injecting dermal filler into the lips. The most notable is the degree of control that is required by the healthcare professional. As discussed above, small amounts of dermal filler must be injected by the healthcare professional in a very controlled manner. This level of control is difficult to achieve using conventional syringes. Simply put, the plunger 806 tends to be somewhat difficult to control with much precision, especially if the syringe 800 is held in one hand (e.g., while the other hand tensions the upper lip or lower lip).

One solution is to use aspirating syringes to inject dermal filler into the lips. Aspirating syringes are increasingly being used across several disciplines. For example, aspirating syringes are commonly used in the practice of dentistry. The term "aspiration" refers to the process of removing fluids or tissue from the body. In an aspirating syringe, the plunger can be pulled back to intentionally remove fluid or tissue to create a small vacuum into which a substance (e.g., dermal filler) can be injected. Normally, this vacuum is created for a short interval of time (e.g., 5-10 seconds) so that the healthcare professional can be sure that the tip of the needle is located in the appropriate spot.

Figure 9:
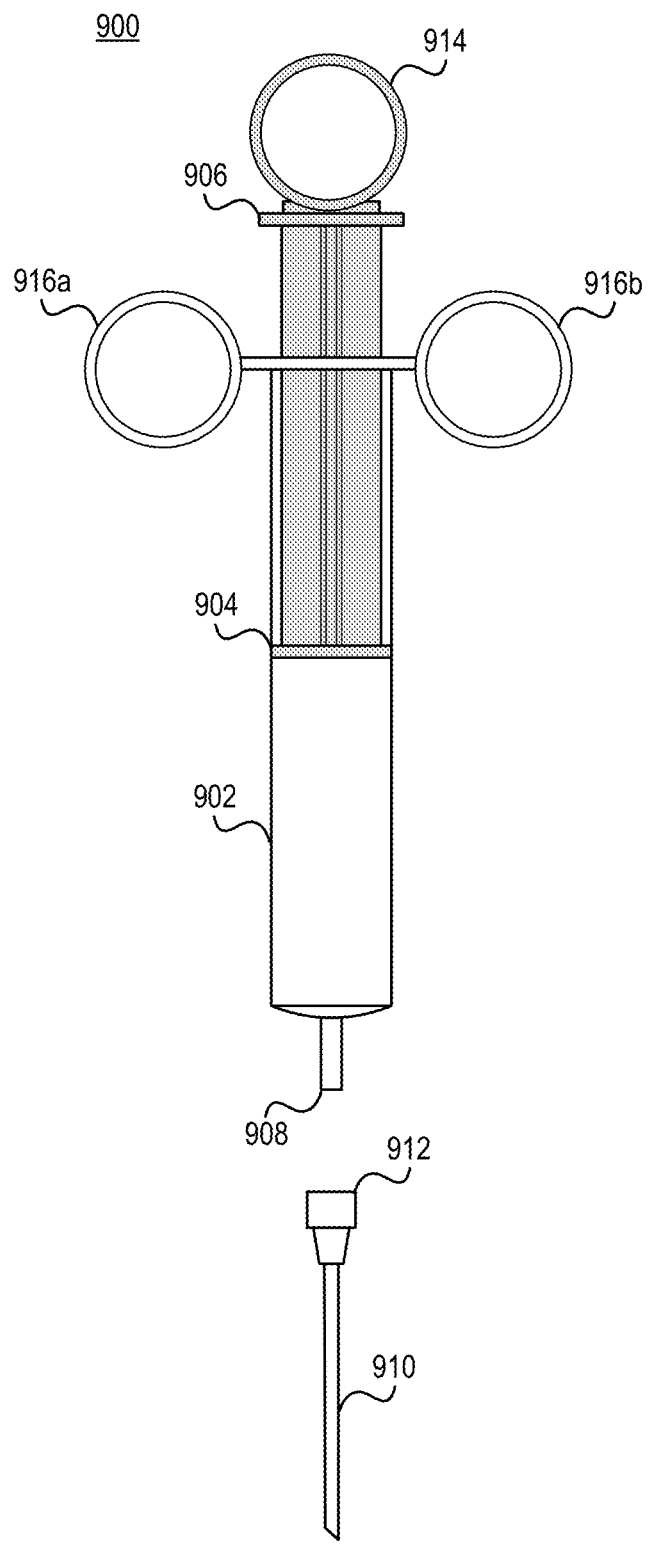
FIG. 9 includes an illustration of an aspirating syringe.

FIG. 9 includes an illustration of an aspirating syringe 900. As can be seen in FIG. 9, the aspirating syringe 900 is similar to the conventional syringe 800 of FIG. 8, with a durable barrel 902, a piston 904, and a plunger 906. At the end of the barrel 902, there is a tip 908 to which a needle 910 (and, more specifically, a needle hub 912) can be connected. However, unlike the conventional syringe 800 of FIG. 8, the aspirating syringe 900 may include a ring 914 that allows the plunger 906 to more easily be drawn upward (i.e., away from the tip 908). This ring 914 may be designed to accommodate the thumb. This ring 914 not only allows the healthcare professional to use the aspirating syringe 900 to aspirate, but also give the healthcare professional greater control over the ejection of substances (e.g., dermal filler) through the tip of the needle 910. To further improve control, some aspirating syringes include a ring 916a (e.g., for the pointer finger or ring finger) that is connected to the barrel 902, and some aspirating syringes include a pair of rings 916a-b (e.g., for the pointer and ring fingers) that are connected to the barrel 902.

Figure 10:
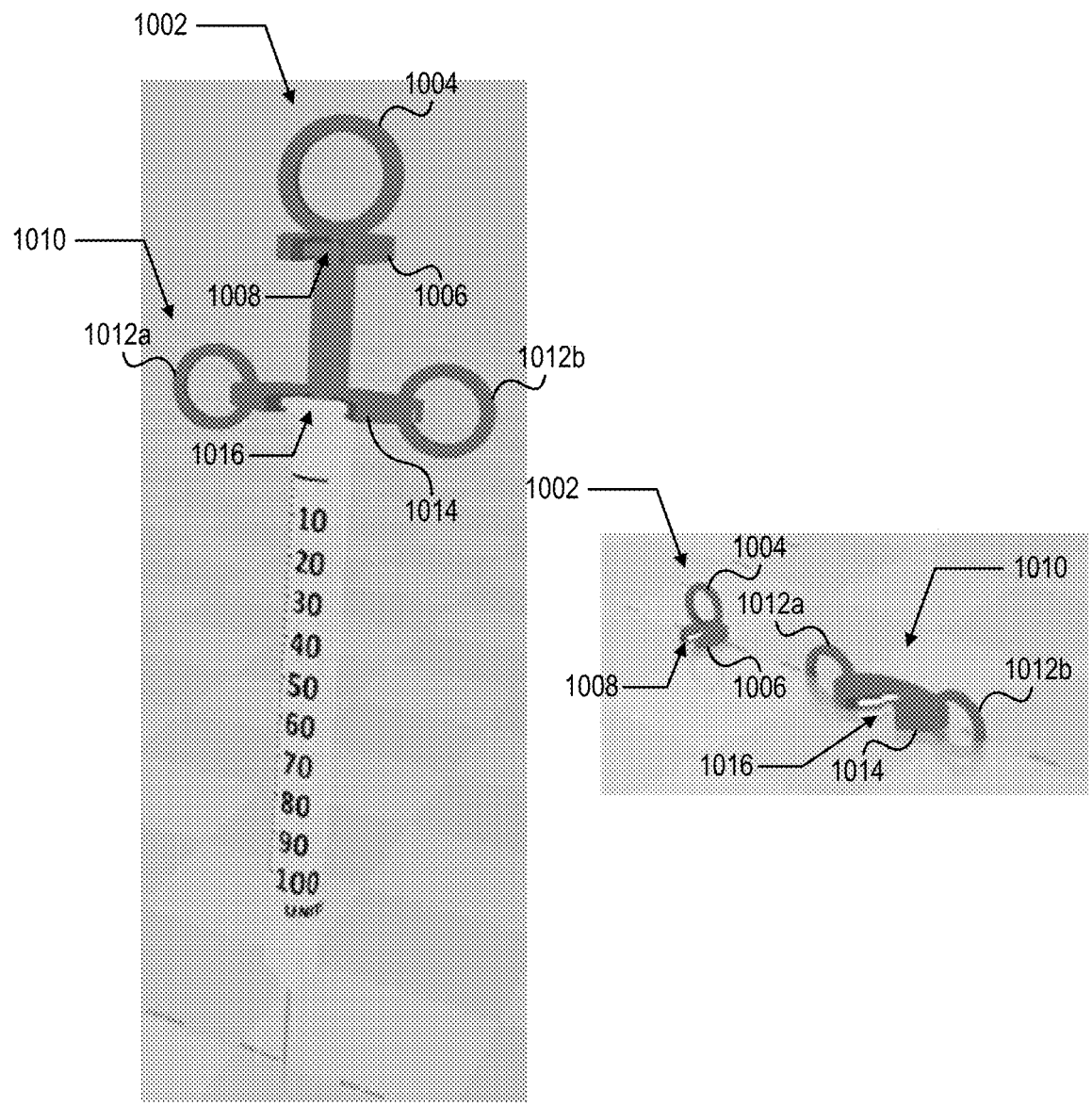
FIG. 10 illustrates several examples of attachment mechanisms (or simply "attachments") that could be secured to a syringe.

Another solution is to secure one or more attachments to a syringe (e.g., a conventional syringe or aspirating syringe) to facilitate the injection of dermal filler into the lips. FIG. 10 illustrates several examples of attachment mechanisms (or simply "attachments") that could be secured to a syringe.

A first type of attachment 1002 is designed to emulate the ring that is found on aspirating syringes. This attachment 1002 can include an annular ring 1004 that is connected to a collar 1006. Normally, the collar 1006 is open along the side opposite the annular ring 1006. This opening 1008 allows the attachment 1002 to be slid onto the plunger as shown in FIG. 10.

A second type of attachment 1010 is designed to emulate the rings that are found on some aspirating syringes. This second type of attachment 1010 can include a pair of annular rings 1012a-b that are connected to a collar 1014. Again, the collar 1014 may be open so as to allow the attachment 1010 to be slid onto the barrel as shown in FIG. 10. Normally, the pair of annular rings 1012a-b are located along opposing sides of the attachment 1010, for example, to accommodate the pointer and ring fingers if the healthcare professional places her thumb through another ring located atop the plunger. This other ring may be provided by the first type of attachment 1002, or this other ring may naturally be part of the syringe (e.g., when the syringe is an aspirating syringe). The opening 1016 may be evenly spaced between the pair of annular rings 1012a-b for structural reasons.

As shown in FIGS. 8-9, convention and aspirating syringes normally include lips along the top of the barrel and the top of the plunger. The collars 1006, 1014 may include channels defined therein that are designed to accommodate these lips. Accordingly, the collar 1006 of the first type of attachment 1002 may be able to slidably engage the plunger when its lip is secured within the channel defined in the collar 1006. Similarly, the collar 1014 of the second type of attachment 1010 may be able to slidably engage the barrel when its lip is secured within the channel defined in the collar 1014.

Those skilled in the art will recognize that a healthcare professional could opt to use the first type of attachment, the second type of attachment, or the first and second types of attachments depending on the nature of the syringe being used for injection. For example, if the healthcare professional is using a conventional syringe, then she may opt to use the first type of attachment and/or the second type of attachment. However, if the healthcare professional is using an aspirating syringe, then a ring may already be present along the top of the plunger. Accordingly, the healthcare professional may only be able to secure the second type of attachment to the aspirating syringe.

Remarks

The foregoing description of various embodiments has been provided for the purposes of illustration and description. It is not intended to be exhaustive or to limit the claimed subject matter to the precise forms disclosed. Many modifications will be apparent to one skilled in the art. Embodiments were chosen in order to best describe the principles of the invention and its practical applications, thereby enabling those skilled in the relevant art to understand the claimed subject matter, the various embodiments, and the various modifications that are suited to the particular uses contemplated.

Although the Detailed Description describes various embodiments, the technology can be practiced in many ways no matter how detailed the Detailed Description appears. Embodiments may vary considerably in their implementation details, while still being encompassed by the present disclosure. Particular terminology used when describing characteristics, features, or aspects of various embodiments should not be taken to imply that the terminology is being redefined herein to be restricted to any specific characteristics, features, or aspects of the technology with which that terminology is associated. In general, the terms used in the claims should not be construed to limit the technology to the embodiments described in the present disclosure, unless those terms are explicitly defined herein. Accordingly, the actual scope of the technology encompasses not only the disclosed embodiments, but also all equivalent ways of practicing or implementing the technology.

The language used in the specification has been principally selected for readability and instructional purposes. It may not have been selected to delineate or circumscribe the claimed subject matter. It is therefore intended that the scope of the technology be limited not by this Detailed Description, but rather by any claims that issue on an application based hereon. The present disclosure is intended to be illustrative, but not limiting, of the scope of the technology as set forth in the following claims.

What is claimed is:

1. A method for lip augmentation, the method comprising:
   orienting a syringe containing a dermal filler so that a tip of a needle is located proximate to an apex point along a vermilion border of an upper lip;
   creating a first series of vertical tunnels in the upper lip by—
      puncturing the upper lip with the tip of the needle so as to form a hole, and
      pushing the needle into the upper lip repeatedly along different linear vectors so as to form the first series of vertical tunnels by repeatedly adjusting an orientation of the syringe while the tip of the needle remains inside the upper lip;
   reinserting the tip of the needle through the hole in the upper lip;
   pushing the needle through a vertical tunnel of the first series of vertical tunnels in the upper lip until the tip of the needle reaches a desired depth;
   causing lateral movement of the tip of the needle toward a nearest oral commissure so as to form a lateral tunnel, wherein said causing is accomplished by applying a lateral force to the syringe of which the needle is a part; and
   injecting the dermal filler into the lateral tunnel while withdrawing the tip of the needle through the lateral tunnel and the vertical tunnel toward the hole,
      wherein for each vertical tunnel in the first series of vertical tunnels, the dermal filler is injected while the tip of the needle is withdrawn toward the hole, and
      wherein the method permits augmentation of an outer surface of the upper lip, so as to increase its volume by expanding sideways while turning the upper lip outward.

2. The method of claim 1, wherein the first series of vertical tunnels are arranged along a vertical plane.

3. The method of claim 1, wherein an angle between a given vertical tunnel and a neighboring vertical tunnel formed prior to the given vertical tunnel is a lowest possible angle that is achievable by a healthcare professional without affecting structural integrity of the neighboring vertical tunnel.

4. The method of claim 1, wherein the desired depth corresponds to an endpoint of the vertical tunnel.

5. The method of claim 1, wherein a depth of the tip of the needle does not change while lateral movement occurs.

6. The method of claim 1, further comprising:
tensioning the upper lip while the dermal filler is injected into the lateral tunnel.

7. The method of claim 1, further comprising:
creating a second series of vertical tunnels in the upper lip by—
locating the tip of the needle nearer the nearest oral commissure than the hole,
puncturing the upper lip with the tip of the needle so as to form a second hole, and
pushing the needle into the upper lip repeatedly along different vectors so as to form the second series of tunnels.

8. The method of claim 7, further comprising:
reinserting the tip of the needle through the second hole in the upper lip;
causing lateral movement of the tip of needle along a portion of the vermilion border so as to form a second lateral tunnel; and
injecting dermal filler into the second lateral tunnel while withdrawing the tip of the needle through the second lateral tunnel toward the second hole.

9. The method of claim 1, further comprising:
locating a tip of a second needle proximate to an intersection of a vermilion border of a lower lip and a central plane that vertically splits the lower lip into left and right parts;
puncturing the lower lip with the tip of the second needle so as to form a second hole;
pushing the second needle into the lower lip so as to form a second vertical tunnel;
causing movement of the tip of the second needle along the central plane toward a mucous membrane inside the lower lip so as to form a horizontal tunnel; and
injecting dermal filler into the horizontal tunnel while withdrawing the tip of the second needle through the horizontal and second vertical tunnels toward the second hole.

10. The method of claim 9, wherein the first needle and the second needle are the same needle.

11. The method of claim 1, further comprising:
locating a tip of a second needle proximate to an intersection of a vermilion border of a lower lip and a central plane that vertically splits the lower lip into left and right parts;
puncturing the lower lip with the tip of the second needle so as to form a second hole;
pushing the second needle into the lower lip repeatedly so as to form a second series of vertical tunnels,
wherein for each vertical tunnel in the second series of vertical tunnels, dermal filler is injected while the tip of the second needle is withdrawn toward the second hole.

12. The method of claim 1, further comprising:
locating a tip of a second needle left adjacent of an intersection of a vermilion border of a lower lip and a central plane that vertically splits the lower lip into left and right parts;
puncturing the lower lip with the tip of the second needle so as to form a second hole;
pushing the second needle into the lower lip so as to form a first vertical tunnel that is angled toward a left apex point along the vermilion border of the upper lip;
injecting dermal filler into the first vertical tunnel while withdrawing the tip of the second needle through the first vertical tunnel toward the second hole;
locating the tip of the second needle right adjacent of the intersection of the vermilion border of the lower lip and the central plane;
puncturing the lower lip with the tip of the second needle so as to form a third hole;
pushing the second needle into the lower lip so as to form a second vertical tunnel that is angled toward a right apex point along the vermilion border of the upper lip; and
injecting dermal filler into the second vertical tunnel while withdrawing the tip of the second needle through the second vertical tunnel toward the third hole.

* * * * *